United States Patent
Fessmann et al.

(10) Patent No.: US 7,091,350 B2
(45) Date of Patent: Aug. 15, 2006

(54) DIAMINOPYRAZOLE DERIVATIVES AND THEIR USE FOR OXIDATION DYEING OF KERATINOUS FIBRES

(75) Inventors: Thilo Fessmann, Aulnay Sous Bois (FR); Eric Terranova, Magagnosc (FR)

(73) Assignee: L'Oreal, (FR)

( * ) Notice: Subject to any disclaimer, the term of this patent is extended or adjusted under 35 U.S.C. 154(b) by 0 days.

(21) Appl. No.: 10/468,300

(22) PCT Filed: Feb. 14, 2002

(86) PCT No.: PCT/FR02/00566

§ 371 (c)(1),
(2), (4) Date: Dec. 4, 2003

(87) PCT Pub. No.: WO02/066440

PCT Pub. Date: Aug. 29, 2002

(65) Prior Publication Data

US 2004/0088802 A1 May 13, 2004

(30) Foreign Application Priority Data

Feb. 21, 2001 (FR) .................................. 01 02309

(51) Int. Cl.
*C07D 231/38* (2006.01)
*C07D 401/04* (2006.01)
*C07D 403/04* (2006.01)
*C07D 403/06* (2006.01)
*C07D 403/14* (2006.01)
*C07D 405/06* (2006.01)
*A61Q 5/10* (2006.01)

(52) U.S. Cl. .................. 544/371; 546/211; 548/215; 548/312.4; 548/364.1; 548/365.7; 548/371.7; 548/372.5; 8/409; 8/423

(58) Field of Classification Search ................ 544/371; 546/211; 548/215, 312.4, 364.1, 365.7, 371.7, 548/372.5; 8/409, 423
See application file for complete search history.

(56) References Cited

U.S. PATENT DOCUMENTS

| 4,823,985 A | 4/1989 | Grollier et al. | 222/1 |
| 5,032,137 A | 7/1991 | Junino et al. | 8/410 |
| 5,061,289 A | 10/1991 | Clausen et al. | 8/405 |
| 5,663,366 A | 9/1997 | Neunhoeffer et al. | 548/371.4 |
| 5,718,731 A * | 2/1998 | Loewe et al. | 8/409 |
| 5,769,902 A * | 6/1998 | Samain | 8/409 |
| 5,785,717 A * | 7/1998 | Maubru et al. | 8/409 |
| 6,740,127 B1 * | 5/2004 | Friess et al. | 8/405 |

FOREIGN PATENT DOCUMENTS

| DE | 38 43 892 | 6/1990 |
| DE | 42 34 885 | 4/1994 |
| DE | 196 46 609 | 5/1998 |
| FR | 2 586 913 | 3/1987 |
| FR | 2 630 438 | 10/1989 |
| WO | WO 98/20847 | 5/1998 |

OTHER PUBLICATIONS

English language Derwent Abstract of DE 196 46 609, May 14, 1998.

* cited by examiner

*Primary Examiner*—Fiona T. Powers
(74) *Attorney, Agent, or Firm*—Finnegan, Henderson, Farabow, Garrett & Dunner, LLP

(57) ABSTRACT

The invention relates to diaminopyrazole derivatives having the following structure (I), wherein $R_1$ represents an alkyl or alkenyl radical bearing at least one substituent selected from among OR, NRR', SR, SOR, $SO_2R$, COOR, CONRR', $PO(OH)_2$, $SO_3X$, NHCONRR, a non-cationic heterocycle, an aryl, a halogen. $R_2$ and $R_3$ are different from H and represent, independently of each other, an alkyl or alkenyl group; $R_2$ and $R_3$, together with the nitrogen atom to which they are attached, can form a heterocycle possibly comprising at least one other heteroatom selected from among N, O and S; $R_2$ and $R_3$ or the heterocycle that they form with the nitrogen to which they are attached can be substituted by at least one substituent defined above. The identical or different R, R' groups are selected from a hydrogen atom, an alkyl or alkenyl group; R and R', together with the nitrogen atom to which they are attached, can form a heterocycle having at least 4 ring members that can contain at least one additional heteroatom selected from among O, N and S. X represents a hydrogen, an alkaline-earth or alkali metal atom or an ammonium group. The invention also relates to the dyeing compositions and the dyeing methods using same

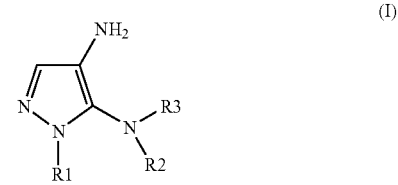

(I)

32 Claims, No Drawings

DIAMINOPYRAZOLE DERIVATIVES AND THEIR USE FOR OXIDATION DYEING OF KERATINOUS FIBRES

The present invention relates to novel diaminopyrazole derivatives, to a composition for the oxidation dyeing of keratin fibers, and in particular of human keratin fibers such as the hair, comprising at least one diaminopyrazole derivative as oxidation base, and to the oxidation dyeing processes using it.

It is known practice to dye keratin fibers, and in particular human hair, with dye compositions containing oxidation dye precursors, in particular ortho- or para-phenylenediamines, ortho-aminophenols or para-aminophenols and heterocyclic compounds such as diaminopyrazole derivatives, which are generally referred to as "oxidation bases". The oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colors.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fiber, which may indeed be differently sensitized (i.e. damaged) between its tip and its root. They must also show good chemical stability in the formulations, and must have a good toxicological profile.

Furthermore, for a certain number of applications, dyes that produce chromatic shades on the hair, in particular the range of red tones, are desired in order to obtain warm shades.

Patent application DE 19 646 609 discloses 4,5-di-aminopyrazole derivatives, which, when used together with various couplers, especially benzoxazines, give chestnut-brown shades with blue, red, violet, aubergine or coppery glints.

However, these dyes do not satisfy all the above requirements.

The Applicant has now discovered, entirely surprisingly and unexpectedly, that it is possible to obtain dyes which are capable of producing powerful, particularly chromatic and bright colorations, in the range of red tones, and which are relatively unselective and have excellent properties of resistance to the various attacking factors to which keratin fibers may be subjected, by using as oxidation base the diaminopyrazoles of the formula (I) below or physiologically acceptable salts thereof.

One subject of the present invention is thus the novel 4,5-diaminopyrazoles having the following structure (I):

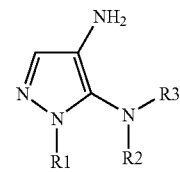

in which
R$_1$ denotes a linear or branched C$_1$–C$_6$ alkyl radical or C$_2$–C$_6$ alkenyl radical, and preferably up to C$_4$, bearing at least one substituent chosen from OR, NRR', SR, SOR, SO$_2$R, COOR, CONRR', PO(OH)$_2$, SO$_3$X, NHCONRR', a non-cationic heterocycle, an aryl and a halogen, R$_2$ and R$_3$ are other than H and denote, independently of each other, a linear or branched, substituted or unsubstituted C$_1$–C$_6$ alkyl or C$_2$–C$_6$ alkenyl group, preferably up to C$_4$, R$_2$ and R$_3$ may form with the nitrogen atom to which they are attached a saturated or unsaturated at least 4-membered heterocycle, optionally comprising at least one further hetero atom chosen from N, O and S, R$_2$ and R$_3$ or the heterocycle that they form with the nitrogen to which they are attached possibly being substituted with at least one substituent chosen from OR, NRR', SR, SOR, SO$_2$R, COOR, CONRR', PO(OH)$_2$, SO$_3$X, NHCONRR', a non-cationic heterocycle, an aryl and a halogen, the groups R and R', which may be identical or different, being chosen from a hydrogen atom and a linear or branched C$_1$–C$_6$ alkyl or C$_2$–C$_6$ alkenyl group, preferably up to C$_4$, R and R' possibly forming with the nitrogen atom to which they are attached an at least 4-membered heterocycle which may contain at least one additional hetero atom chosen from O, N and S, these groups R and R' or the heterocycle that they form with the nitrogen to which they are attached possibly being unsubstituted or substituted; X denotes a hydrogen, an alkali metal or alkaline-earth metal atom or an ammonium group, and also the physiologically acceptable salts thereof.

When R and R' are substituted with one or more substituents, these substituents are preferably chosen from OR", NR"R'", SR", SOR", SO$_2$R", COOR", CONR"R'", PO(OH)$_2$, SO$_3$X, NHCONR"R'", a non-cationic heterocycle, an aryl and a halogen, in which R" and R'" denote hydrogen or linear or branched C$_1$–C$_6$ alkyl or C$_2$–C$_6$ alkenyl, preferably up to C$_4$.

The term "heterocycle" preferably denotes hydrocarbon-based 4- to 6-membered rings interrupted with at least one hetero atom, preferably one to three hetero atoms, chosen from O, N and S and possibly being substituted, for example with the substituents as defined above. Mention may be made of pyrazole, imidazole, piperazine, pyrrolidine, pyrrole, piperidine, imidazolidine, etc. derivatives.

The term "aryl" preferably denotes phenyl.

The term "halogen" preferably denotes Cl, Br or I.

R$_1$ preferably denotes a linear or branched C$_1$–C$_6$ alkyl radical, substituted with an SO$_3$H, COOH, OH, C$_1$–C$_4$ alkoxy, NH$_2$ or NRR' group in which R and R' denote, independently of each other, C$_1$–C$_4$ alkyl optionally substituted with OH, C$_1$–C$_4$ alkoxy optionally substituted with OH, or NR"R'" in which R" and R'" denote, independently of each other, hydrogen or a $C_1$–$C_4$ alkyl group; R and R' may form with the nitrogen atom to which they are attached a 5- to 6-membered heterocycle optionally interrupted with one or two additional hetero atoms chosen from O and N.

$R_2$ and/or $R_3$, which may be identical or different, preferably denote $C_1$–$C_6$ alkyl optionally substituted with OH, $NH_2$, $C_1$–$C_6$ alkoxy or COOH; $R_2$ and $R_3$ may form with the nitrogen atom to which they are attached a 5- or 6-membered heterocycle optionally comprising one or 2 hetero atoms chosen from O and N, these heterocycles optionally being substituted with one or more CHO, $CONH_2$, OH, $NH_2$, phenyl, saturated or unsaturated 5- or 6-membered heterocycle optionally comprising from one to 3 hetero atom(s) such as O, N or S, or $CO_2R''$ group(s) in which R'' denotes H or $C_1$–$C_4$ alkyl.

A subject of the invention is also the physiologically acceptable acid or base salts of the compounds of formula (I), such as the hydrochlorides, hydrobromides, sulfates, tartrates, lactates or acetates, or the salts obtained with sodium hydroxide, potassium hydroxide, ammonia, amines or alkanolamines.

A subject of the invention is also a composition for the oxidation dyeing of keratin fibers, and in particular of human keratin fibers such as the hair, characterized in that it contains, in a medium that is suitable for dyeing, as oxidation base, at least one 4,5-diaminopyrazole of formula (I) above, or physiologically acceptable acid or base salts thereof.

As mentioned above, the colorations obtained with the oxidation dye composition in accordance with the invention are powerful, particularly bright and chromatic. They in particular produce shades that are more red. Furthermore, they show excellent properties of resistance with respect to the action of various external agents (light, bad weather, washing, permanent-waving, perspiration and friction).

A subject of the invention is also a process for the oxidation dyeing of keratin fibers using such a dye composition.

As examples of diaminopyrazoles of formula (I) according to the invention, mention may be made of the following compounds:

| Structure | Name | Structure | Name | Structure | Name |
|---|---|---|---|---|---|
| 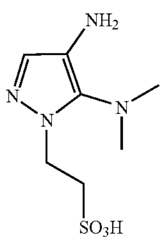 | 2-(4-amino-5-dimethyl-amino-pyrazol-1-yl)ethane-sulfonic acid | 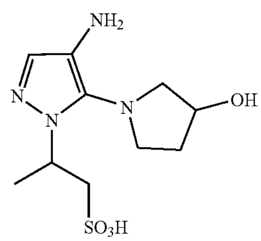 | 2-[4-amino-5-(3-hydroxy-pyrrolidin-1-yl)-pyrazol-1-yl]propane-1-sulfonic acid | 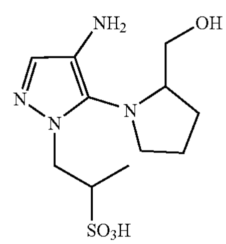 | 1-[4-amino-5-(2-hydroxy-methyl-pyrrolidin-1-yl)-pyrazol-1-yl]propane-2-sulfonic acid |
| 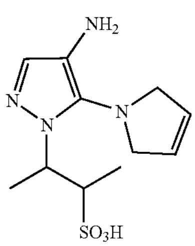 | 3-[4-amino-5-(2,5-dihydro-pyrrol-1-yl)pyrazol-1-yl]-butane-2-sulfonic acid | 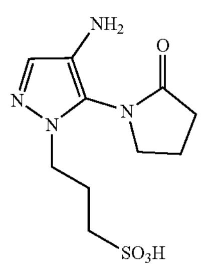 | 3-[4-amino-5-(2-oxo-pyrrolidin-1-yl)-pyrazol-1-yl]propane-1-sulfonic acid | 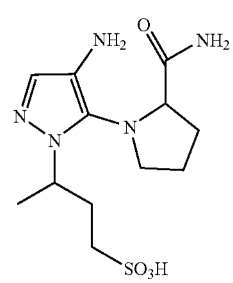 | 3-[4-amino-5-(2-carbamoyl-pyrrolidin-1-yl)-pyrazol-1-yl]butane-1-sulfonic acid |
| 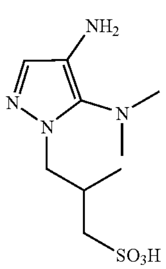 | 3-(4-amino-5-dimethyl-amino-pyrazol-1-yl)-2-methyl-propane-1-sulfonic acid | 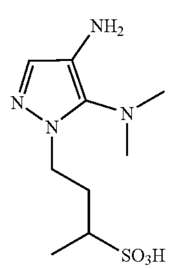 | 4-(4-amino-5-dimethyl-amino-pyrazol-1-yl)butane-2-sulfonic acid | 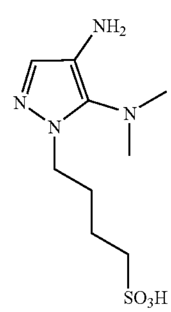 | 4-[4-amino-5-dimethyl-amino-pyrazol-1-yl)butane-1-sulfonic acid |

-continued

| Structure | Name | Structure | Name | Structure | Name |
|---|---|---|---|---|---|
| | 4-(4-amino-5-dimethyl-amino-pyrazol-1-yl)-3-methyl-butane-1-sulfonic acid | | 5-(4-amino-5-dimethyl-amino-pyrazol-1-yl)-4-methyl-pentane-1-sulfonic acid | | 2-{4-amino-5-[bis(2-hydroxy-ethyl)-amino]-pyrazol-1-yl}ethane-sulfonic acid |
| | {4-amino-5-[bis(2-methoxy-ethyl)-amino]-pyrazol-1-yl}ethane-sulfonic acid | | {[4-amino-2-(2-sulfo-ethyl)-2H-pyrazol-3-yl]methyl-amino}-acetic acid | | 2-{4-amino-5-[bis(2-amino-ethyl)-amino]-pyrazol-1-yl}ethane-sulfonic acid |
| | 3-(4-amino-5-dimethyl-amino-pyrazol-1-yl)propane-1-sulfonic acid | | 3-[4-amino-5-(ethyl-methyl-amino)-pyrazol-1-yl]propane-1-sulfonic acid | | 2-{4-amino-5-[(2-hydroxy-ethyl)-methyl-amino]-pyrazol-1-yl}propane-1-sulfonic acid |
| | 2-{4-amino-5-[ethyl-(2-methoxy-ethyl)-amino]-pyrazol-1-yl}propane-1-sulfonic acid | | {[4-amino-2-(3-sulfo-propyl)-2H-pyrazol-3-yl]methyl-amino}-acetic acid | | 3-{4-amino-5-[(2-amino-ethyl)-(2-methoxy-ethyl)-amino]-pyrazol-1-yl}propane-1-sulfonic acid |
| | 2-[4-amino-5-(3-methyl-pyrrolidin-1-yl)-pyrazol-1-yl]-acetamide | | 2-[4-amino-5-(ethyl-methyl-amino)-pyrazol-1-yl]propion-amide | | 3-(4-amino-5-pyrrolidin-1-yl-pyrazol-1-yl)-butyramide |

-continued

| Structure | Name | Structure | Name | Structure | Name |
|---|---|---|---|---|---|
| | 3-(4-amino-5-dimethyl-amino-pyrazol-1-yl)-butyramide | | 3-[4-amino-5-(2-formyl-pyrrolidin-1-yl)pyrazol-1-yl]-2-methyl-propionamide | | 1-[4-amino-2-(3-carbamoyl-propyl)-2H-pyrazol-3-yl]pyrrolidine-2-carboxamide |
| | 4-[4-amino-5-(3,4-dihydroxy-pyrrolidin-1-yl)-pyrazol-1-yl]-3-methyl-butyramide | | 5-(4-amino-5-dimethyl-amino-pyrazol-1-yl)-pentanamide | | 5-(4-amino-5-dimethyl-amino-pyrazol-1-yl)-4-methyl-pentanamide |
| | 6-(4-amino-5-dimethyl-amino-pyrazol-1-yl)hexanamide | | 2-(4-amino-5-dimethyl-amino-pyrazol-1-yl)-acetamide | | 2-(4-amino-5-diethyl-amino-pyrazol-1-yl)-acetamide |
| | 2-{4-amino-5-[bis(2-hydroxy-ethyl)-amino]-pyrazol-1-yl}-acetamide | | 2-{4-amino-5-[bis(2-amino-ethyl)-amino]-pyrazol-1-yl}-acetamide | | [(4-amino-2-carbamoyl-methyl-2H-pyrazol-3-yl)methyl-amino}-acetic acid |
| | 3-(4-amino-5-dimethyl-amino-pyrazol-1-yl)propionamide | | 3-(4-amino-5-diethyl-amino-pyrazol-1-yl)propionamide | | 3-{4-amino-5-[bis(2-hydroxy-ethyl)-amino]-pyrazol-1-yl}propionamide |

-continued

| Structure | Name | Structure | Name | Structure | Name |
|---|---|---|---|---|---|
| | 3-{4-amino-5-[(2-amino-ethyl)-(2-methoxy-ethyl)-amino]-pyrazol-1-yl}propion-amide | | 3-{4-amino-5-[bis(2-amino-ethyl)-amino]-pyrazol-1-yl}propion-amide | | {[4-amino-2-(2-carbamoyl-ethyl)-2H-pyrazol-3-yl]methyl-amino}-acetic acid |
| | [4-amino-5-(2,5-dihydro-pyrrol-1-yl)pyrazol-1-yl]acetic acid | | 2-(4-amino-5-dimethyl-amino-pyrazol-1-yl)-propionic acid | | 3-(4-amino-5-diethyl-amino-pyrazol-1-yl)-propionic acid |
| | methyl 1-[4-amino-2-(2-carboxy-1-methyl-ethyl)-2H-pyrazol-3-yl]pyrroli-dine-2-carboxylate | | 3-(4-amino-5-pyrrolidin-1-yl-pyrazol-1-yl)-2-methyl-propionic acid | | 4-[4-amino-5-(3-amino-pyrrolidin-1-yl)-pyrazol-1-yl]butyric acid |
| | 4-(4-amino-5-dimethyl-amino-pyrazol-1-yl)-3-methyl-butyric acid | | 5-(4-amino-5-dimethyl-amino-pyrazol-1-yl)-pentanoic acid | | 5-(4-amino-5-dimethyl-amino-pyrazol-1-yl)-3-methyl-pentanoic acid |
| | 6-(4-amino-5-pyrrolidin-1-yl-pyrazol-1-yl)hexanoic acid | | (4-amino-5-dimethyl-amino-pyrazol-1-yl)acetic acid | | (4-amino-5-diethyl-amino-pyrazol-1-yl)acetic acid |

-continued

| Structure | Name | Structure | Name | Structure | Name |
|---|---|---|---|---|---|
| | {4-amino-5-[bis(2-hydroxyethyl)-amino]-pyrazol-1-yl}acetic acid | | [4-amino-5-(carboxymethyl-methyl-amino)-pyrazol-1-yl]acetic acid | | {4-amino-5-[bis(2-aminoethyl)-amino]-pyrazol-1-yl}acetic acid |
| | 1-(2-(dimethyl-amino-ethyl)-5-piperidin-1-yl-1H-pyrazol-4-ylamine | | 1-(2-dimethyl-amino-1-methyl-ethyl)-5-pyrrolidin-1-yl-1H-pyrazol-4-ylamine | | 1-(2-dimethyl-amino-propyl)-5-pyrrolidin-1-yl-1H-pyrazol-4-ylamine |
| | 1-(2-dimethyl-amino-1-methyl-propyl)-5-(3-methyl-pyrrolidin-1-yl)-1H-pyrazol-4-ylamine | | 1-(3-dimethyl-amino-propyl)-5-(3-phenyl-pyrrolidin-1-yl)-1H-pyrazol-4-ylamine | | 1-(3-dimethyl-amino-1-methyl-propyl)-5-(3-pyridin-4-yl-pyrrolidin-1-yl)-1H-pyrazol-4-ylamine |
| | 2-(3-dimethyl-amino-2-methyl-propyl)-N3,N3-dimethyl-2H-pyrazole-3,4-diamine | | 2-(3-dimethyl-amino-butyl)-N3,N3-diethyl-2H-pyrazole-3,4-diamine | | 5-(2,5-dihydro-pyrrol-1-yl)-1-(4-dimethyl-amino-butyl)-1H-pyrazol-4-ylamine |
| | 2-(4-dimethyl-amino-3-methyl-butyl)-N3,N3-dimethyl-2H-pyrazole-3,4-diamine | | 2-[[4-amino-2-(2-dimethyl-amino-ethyl)-2H-pyrazol-3-yl]-(2-hydroxy-ethyl)-amino]-ethanol | | {[4-amino-2-(2-dimethyl-amino-ethyl)-2H-pyrazol-3-yl]methyl-amino}-acetic acid |

| Structure | Name | Structure | Name | Structure | Name |
|---|---|---|---|---|---|
| 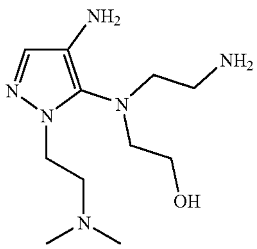 | 2-[[4-amino-2-(2-dimethyl-amino-ethyl)-2H-pyrazol-3-yl]-(2-amino-ethyl)-amino]-ethanol | 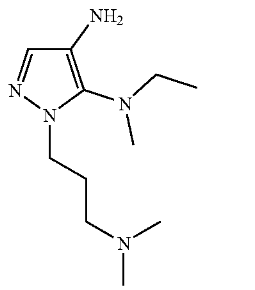 | 2-(3-dimethyl-amino-propyl)-N3-ethyl-N3-methyl-2H-pyrazole-3,4-diamine | 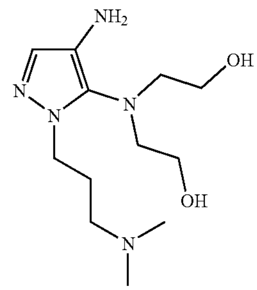 | 2-[[4-amino-2-(3-dimethyl-amino-propyl)-2H-pyrazol-3-yl]-(2-hydroxy-ethyl)-amino]-ethanol |
| 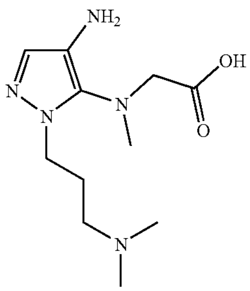 | {[4-amino-2-(3-dimethyl-amino-propyl)-2H-pyrazol-3-yl]methyl-amino}-acetic acid | 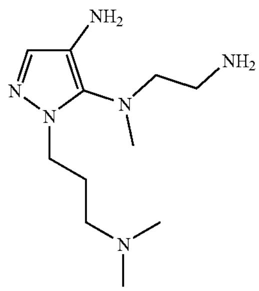 | N3-(2-amino-ethyl)-2-(3-di-methyl-amino-propyl)-N3-methyl-2H-pyrazole-3,4-diamine | 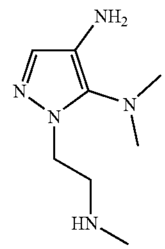 | N3,N3-dimethyl-2-(2-methyl-amino-ethyl)-2H-pyrazole-3,4-diamine |
| 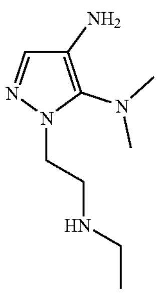 | 2-(2-ethyl-amino-ethyl)-N3,N3-di-methyl-2H-pyrazole-3,4-diamine | 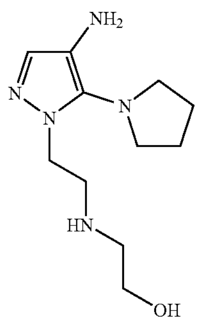 | 2-[2-(4-amino-5-pyrrolidin-1-yl-pyrazol-1-yl)ethyl-amino]-ethanol | 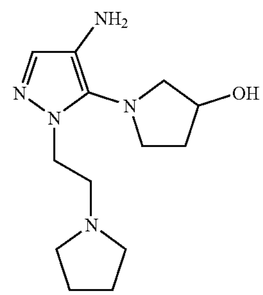 | 1-[4-amino-2-(2-pyrrolidin-1-ylethyl)-2H-pyrazol-3-yl]-pyrrolidin-3-ol |
| 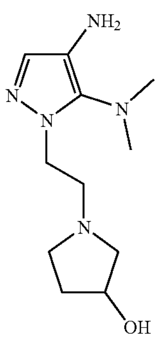 | 1-[2-(4-amino-5-dimethyl-amino-pyrazol-1-yl)ethyl]-pyrrolidin-3-ol | 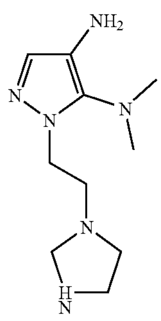 | 2-(2-imidazole-din-1-yl-ethyl)-N3,N3-di-methyl-2H-pyrazole-3,4-diamine | 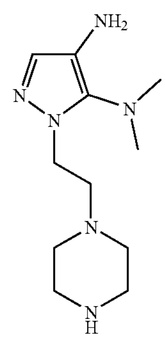 | N3,N3-dimethyl-2-(2-piperazin-1-ylethyl)-2H-pyrazole-3,4-diamine |
| 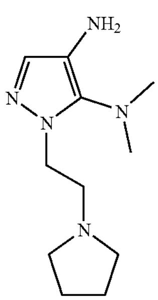 | N3,N3-dimethyl-2-(2-pyrrolidin-1-ylethyl)-2H-pyrazole-3,4-diamine | | | | |

| Structure | Name | Structure | Name | Structure | Name |
|---|---|---|---|---|---|
| | 5-imidazolidin-1-yl-1-(2-methoxy-ethyl)-1H-pyrazol-4-ylamine | | 1-[4-amino-2-(2-methoxy-1-methyl-ethyl)-2H-pyrazol-3-yl]-pyrrolidin-3-ol | | |
| | 2-(2-methoxy-1-methyl-propyl)-N3,N3-dimethyl-2H-pyrazole-3,4-diamine | | 1-(3-methoxy-propyl)-5-piperidin-1-yl-1H-pyrazol-4-ylamine | | 2-(3-methoxy-butyl)-N3,N3-dimethyl-2H-pyrazole-3,4-diamine |
| | 2-(4-methoxy-butyl)-N3,N3,-dimethyl-2H-pyrazole-3,4-diamine | | 2-(4-methoxy-3-methyl-butyl)-N3,N3-dimethyl-2H-pyrazole-3,4-diamine | | 2-(5-methoxy-pentyl)-N3,N3-dimethyl-2H-pyrazole-3,4-diamine |
| | N3,N3-diethyl-2-(2-methoxy-ethyl)-2H-pyrazole-3,4-diamine | | 2-[[4-amino-2-(2-methoxy-ethyl)-2H-pyrazol-3-yl]-(2-hydroxy-ethyl)-amino]-ethanol | | 2,N3,N3-tris(2-methoxy-ethyl)-2H-pyrazole-3,4-diamine |
| | methyl{[4-amino-2-(2-methoxy-ethyl)-2H-pyrazol-3-yl]methyl-amino}-acetate | | N3,N3-bis(2-amino-ethyl)-2-(2-methoxy-ethyl)-2H-pyrazole-3,4-diamine | | 1-[4-amino-2-(3-methoxy-propyl)-2H-pyrazol-3-yl]pyrrolidine-3,4-diol |

-continued

| Structure | Name | Structure | Name | Structure | Name |
|---|---|---|---|---|---|
| 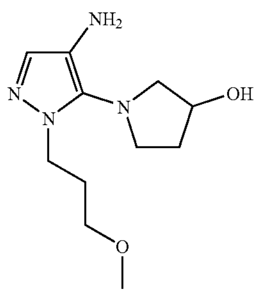 | 1-[4-amino-2-(3-methoxy-propyl)-2H-pyrazol-3-yl]-pyrrolidin-3-ol | 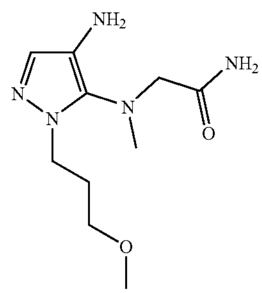 | 2-{[4-amino-2-(3-methoxy-propyl)-2H-pyrazol-3-yl]methyl-amino}-acetamide | 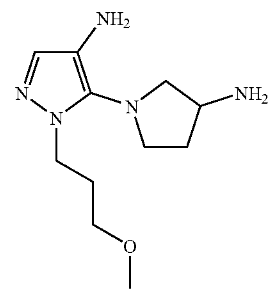 | 5-(3-amino-pyrrolidin-1-yl)-1-(3-methoxy-propyl)-1H-pyrazol-4-ylamine |
| | 2-[2-(2-methoxy-ethoxy)-ethyl]-N3,N3-dimethyl-2H-pyrazole-3,4-diamine | | 2-[2-(2-amino-ethoxy)-ethyl]-N3,N3-dimethyl-2H-pyrazole-3,4-diamine | | 2-[2-(2-dimethyl-amino-ethoxy)ethyl]-N3,N3-dimethyl-2H-pyrazole-3,4-diamine |
| | N3,N3-dimethyl-2-(tetrahydrofuran-2-yl-methyl)-2H-pyrazole-3,4-diamine | | N3,N3,-dimethyl-2-(tetrahydropyran-2-yl-methyl)-2H-pyrazole-3,4-diamine | | 2-[2-(2-methoxy-ethoxy)-ethyl]-N3,N3-dimethyl-2H-pyrazole-3,4-diamine |
| 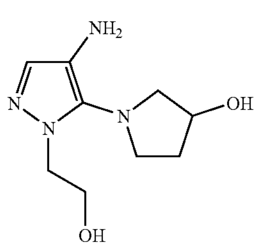 | 1-[4-amino-2-(2-hydroxy-ethyl)-2H-pyrazol-3-yl]-pyrrolidin-3-ol | 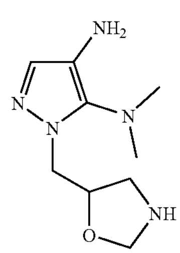 | N3,N3-dimethyl-2-oxazolidin-5-ylmethyl-2H-pyrazole-3,4-diamine | | |

The diaminopyrazoles of formula (I) that are preferred according to the invention have the following structures:

| Structure | Name | Structure | Name | Structure | Name |
|---|---|---|---|---|---|
| 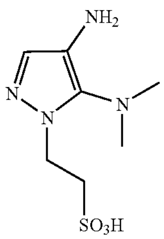 | 2-(4-amino-5-dimethyl-amino-pyrazol-1-yl)ethane-sulfonic acid | 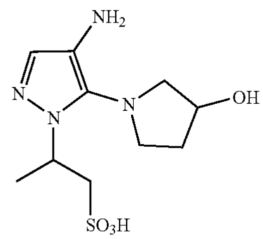 | 2-[4-amino-5-(3-hydroxy-pyrrolidin-1-yl)-pyrazol-1-yl]propane-1-sulfonic acid | 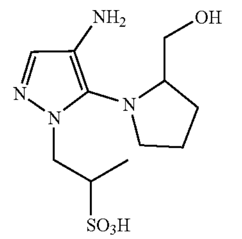 | 1-[4-amino-5-(2-hydroxy-methyl-pyrrolidin-1-yl)-pyrazol-1-yl]propane-2-sulfonic acid |
| 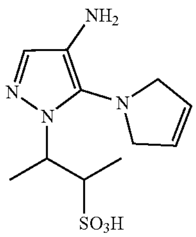 | 3-[4-amino-5-(2,5-dihydro-pyrrol-1-yl)pyrazol-1-yl]-butane-2-sulfonic acid | | | | |
| 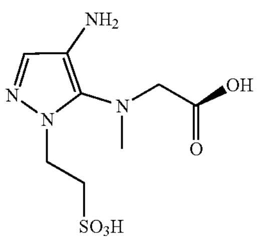 | {[4-amino-2-(2-sulfo-ethyl)-2H-pyrazol-3-yl]methyl-amino}-acetic acid | 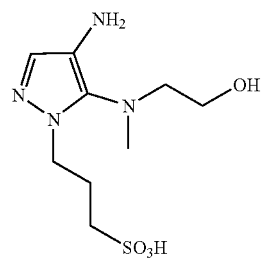 | 2-{4-amino-5-[(2-hydroxy-ethyl)-methyl-amino]-pyrazol-1-yl}propane-1-sulfonic acid | 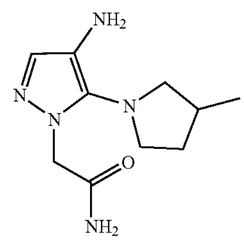 | 2-[4-amino-5-(3-methyl-pyrrolidin-yl]-acetamide |
| 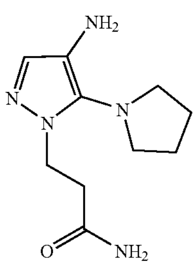 | 3-(4-amino-5-pyrrolidin-1-yl-pyrazol-1-yl)-butyramide | 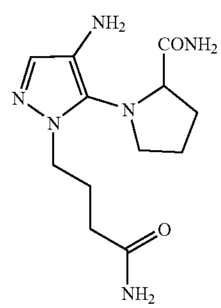 | 1-[4-amino-2-(3-carbamoyl-propyl)-2H-pyrazol-3-yl]pyrrolidine-2-carboxamide | 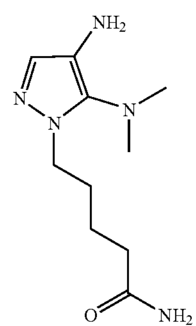 | 5-(4-amino-5-dimethyl-amino-pyrazol-1-yl)-pentanamide |
| 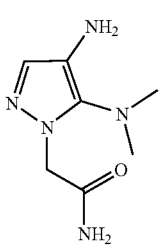 | 2-(4-amino-5-dimethyl-amino-pyrazol-1-yl)-acetamide | 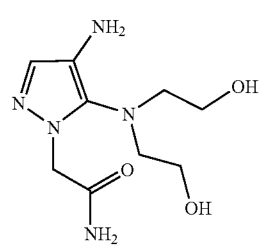 | 2-{4-amino-5-[bis(2-hydroxy-ethyl)-amino]-pyrazol-1-yl}-acetamide | 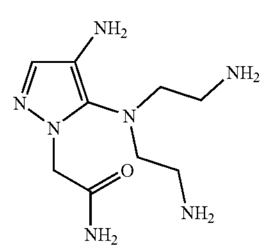 | 2-{4-amino-5-[bis(2-amino-ethyl)-amino]-pyrazol-1-yl}-acetamide |

-continued

| Structure | Name | Structure | Name | Structure | Name |
|---|---|---|---|---|---|
| 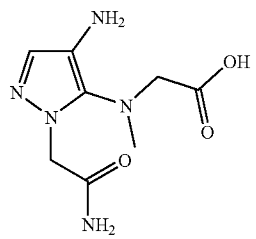 | [(4-amino-2-carbamoyl-methyl-2H-pyrazol-3-yl)methyl-amino]-acetic acid | 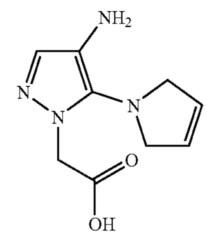 | [4-amino-5-(2,5-dihydro-pyrrol-1-yl)pyrazol-1-yl]acetic acid | 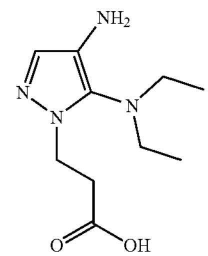 | 3-(4-amino-5-diethyl-amino-pyrazol-1-yl)-propionic acid |
| | 4-[4-amino-5-(3-amino-pyrrolidin-1-yl)-yl]butyric acid | | 5-(4-amino-5-dimethyl-amino-pyrazol-1-yl)-pentanoic acid | | 6-(4-amino-5-pyrrolidin-1-yl-pyrazol-1-yl)hexanoic acid |
| 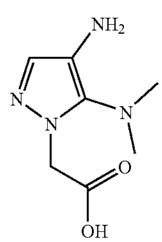 | (4-amino-5-dimethyl-amino-pyrazol-1-yl)acetic acid | 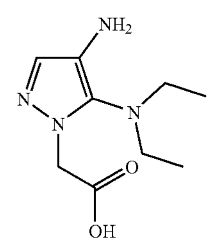 | (4-amino-5-diethyl-amino-pyrazol-1-yl)acetic acid | 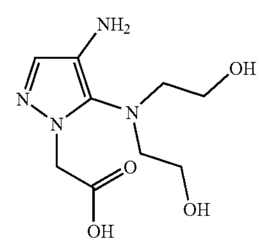 | {4-amino-5-[bis(2-hydroxy-ethyl)-amino]-pyrazol-1-yl}acetic acid |
| 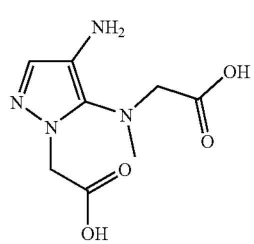 | [4-amino-5-(carboxy-methyl-methyl-amino)-pyrazol-1-yl]acetic acid | 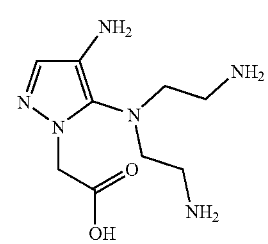 | {4-amino-5-[bis(2-amino-ethyl)-amino]-pyrazol-1-yl}acetic acid | 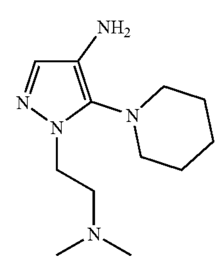 | 1-(2-(dimethyl-amino-ethyl)-5-piperidin-1-yl-1H-pyrazol-4-ylamine |
| 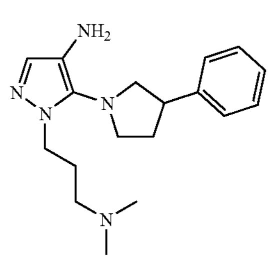 | 1-(3-dimethyl-amino-propyl)-5-(3-phenyl-pyrrolidin-1-yl)-1H-pyrazol-4-ylamine | 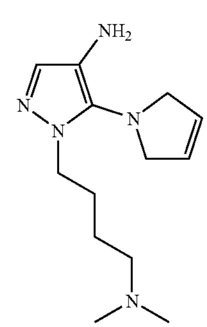 | 5-(2,5-dihydro-pyrrol-1-yl)-1-(4-dimethyl-amino-butyl)-1H-pyrazol-4-ylamine | 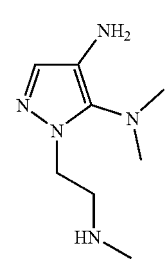 | N3,N3-dimethyl-2-(2-methyl-amino-ethyl)-2H-pyrazole-3,4-diamine |

-continued

| Structure | Name | Structure | Name | Structure | Name |
|---|---|---|---|---|---|
| 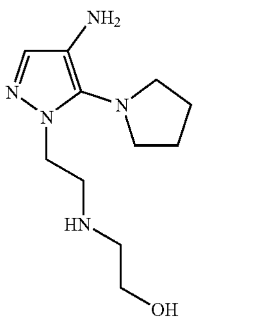 | 2-[2-(4-amino-5-pyrrolidin-1-yl-pyrazol-1-yl)ethyl-amino]-ethanol | 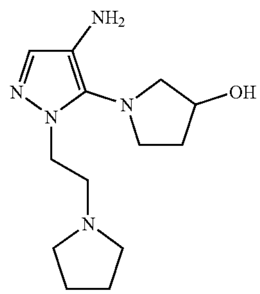 | 1-[4-amino-2-(2-pyrrolidin-1-ylethyl)-2H-pyrazol-3-yl]-pyrrolidin-3-ol | 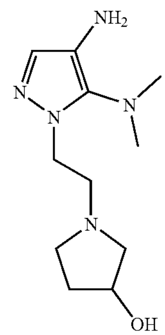 | 1-[2-(4-amino-5-dimethyl-amino-pyrazol-1-yl)ethyl]-pyrrolidin-3-ol |
| | 2-(2-imidazole-din-1-yl-ethyl)-N3,N3-di-methyl-2H-pyrazole-3,4-diamine | | N3,N3-dimethyl-2-(2-piperazin-1-ylethyl)-2H-pyrazole-3,4-diamine | | 5-imidaz-olidin-1-yl-1-(2-methoxy-ethyl)-1H-pyrazol-4-ylamine |
| 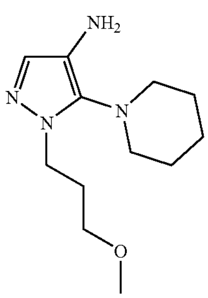 | 1-(3-methoxy-propyl)-5-piperidin-1-yl-1H-pyrazol-4-ylamine | 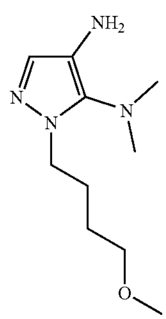 | 2-(4-methoxy-butyl)-N3,N3,-dimethyl-2H-pyrazole-3,4-diamine | 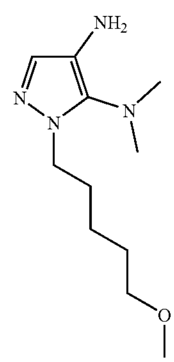 | 2-(5-methoxy-pentyl)-N3,N3-dimethyl-2H-pyrazole-3,4-diamine |
| 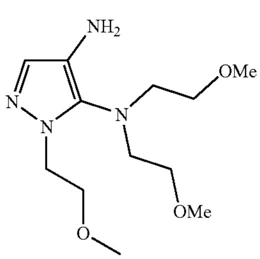 | 2,N3,N3-tris(2-methoxy-ethyl)-2H-pyrazole-3,4-diamine | 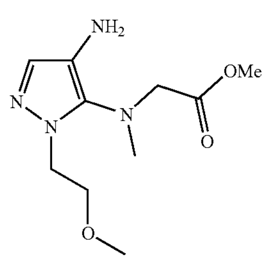 | methyl{[4-amino-2-(2-methoxy-ethyl)-2H-pyrazol-3-yl]methyl-amino}-acetate | | |
| | 1-[4-amino-2-(2-methoxy-propyl)-2H-pyrazol-3-yl]-pyrrolidin-3-ol | | 2-{[4-amino-2-(3-methoxy-propyl)-2H-pyrazol-3-yl]methyl-amino}-acetamide | | 5-(3-amino-pyrrolidin-1-yl)-1-(3-methoxy-propyl)-1H-pyrazol-4-ylamine |

-continued

| Structure | Name | Structure | Name | Structure | Name |
|---|---|---|---|---|---|
| | 2-[2-(2-methoxy-ethoxy)-ethyl]-N3,N3-dimethyl-2H-pyrazole-3,4-diamine | | 2-[2-(2-amino-ethoxy)-ethyl]-N3,N3-dimethyl-2H-pyrazole-3,4-diamine | | 2-[2-(2-dimethyl-amino-ethoxy)ethyl]-N3,N3-dimethyl-2H-pyrazole-3,4-diamine |
| | N3,N3-dimethyl-2-(tetra-hydrofuran-2-yl-methyl)-2H-pyrazole-3,4-diamine | | N3,N3,-dimethyl-2-(tetra-hydropyran-2-yl-methyl)-2H-pyrazole-3,4-diamine | | 2-[2-(2-methoxy-ethoxy)-ethyl]-N3,N3-dimethyl-2H-pyrazole-3,4-diamine |
| | 1-[4-amino-2-(2-hydroxy-ethyl)-2H-pyrazol-3-yl]-pyrrolidin-3-ol | | | | |

The diaminopyrazoles of formula (I) that are more particularly preferred according to the invention are:

1-[4-Amino-2-(2-hydroxyethyl)-2H-pyrazol-3-yl]-pyrrolidin-3-ol
2-(4-Amino-5-dimethylaminopyrazol-1-yl)ethane-sulfonic acid
3-(4-Amino-5-pyrrolidin-1-ylpyrazol-1-yl)-butyramide
2-{4-Amino-5-[bis(2-hydroxyethyl)amino]pyrazol-1-yl}acetamide
(4-Amino-5-dimethylaminopyrazol-1-yl)acetic acid
1-(2-Dimethylaminoethyl)-5-piperidin-1-yl-1H-pyrazol-4-ylamine
N3,N3-Dimethyl-2-(2-methylaminoethyl)-2H-pyrazole-3,4-diamine
1-[2-(4-Amino-5-dimethylaminopyrazol-1-yl)ethyl]-pyrrolidin-3-ol
5-Imidazolidin-1-yl-1-(2-methoxyethyl)-1H-pyrazol-4-ylamine
2,N3,N3-Tris-(2-methoxyethyl)-2H-pyrazole-3,4-diamine or the addition physiologically acceptable acid or base salt.

The diaminopyrazoles of formula (I) according to the invention are prepared, for example, according to the following general preparation method:

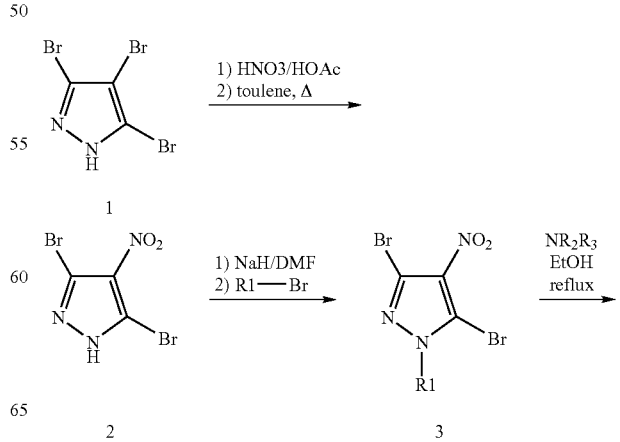

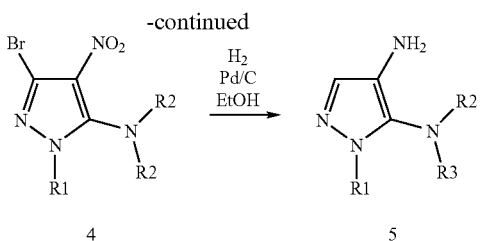

The synthetic approach shown below is described in the literature up to intermediate (2) (J. H. P. Juffermanns, C. L.; Habraken; J. Org. Chem., 1986, 51, 4656; Klebe et al., Synthesis, 1973, 294; R. Hüttel, F. Büchele; Chem. Ber., 1955, 88, 1586). The alkylation and the amination to obtain the compounds of the type (5) of formula (I) according to the invention are mentioned, for example, in document DE 42 34 885.

The dye composition according to the invention especially contains from 0.001% to 10% by weight, preferably from 0.05% to 6% by weight and even more preferably from 0.1% to 3% by weight of at least one diaminopyrazole of formula (I) or of the salts thereof.

The dye composition in accordance with the invention may also contain, in addition to the diaminopyrazole(s) defined above, at least one additional oxidation base that may be chosen from the oxidation bases conventionally used in oxidation dyeing and among which mention may be made especially of para-phenylenediamines, bis(phenyl)alkylenediamines, para-aminophenols, ortho-aminophenols and heterocyclic bases other than the 4,5-diaminopyrazole used in accordance with the invention.

Among the para-phenylenediamines that may be mentioned more particularly, for example, are para-phenylenediamine, para-tolylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis (β-hydroxyethyl)-para-phenylenediamine, 4-amino-N-(β-methoxyethyl)aniline and the para-phenylenediamines described in French patent application FR 2 630 438, and the addition salts thereof.

Among the bis(phenylalkylenediamines that may be mentioned more particularly, for example, are N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof.

Among the heterocyclic bases that may be mentioned more particularly, for example, are pyridine derivatives, pyrimidine derivatives, pyrazolo[1,5-a]pyrimidine derivatives, pyrazolo[1,5-a]pyridine derivatives, pyrazole derivatives other than the diaminopyrazoles of formula (I) used in accordance with the invention, and the addition salts thereof.

When they are used, these additional oxidation bases preferably represent from 0.0005% to 12% by weight relative to the total weight of the dye composition and even more preferably from 0.005% to 6% by weight relative this weight.

The oxidation dye compositions in accordance with the invention may also contain at least one coupler and/or at least one direct dye, especially to modify the shades or to enrich them with glints.

The couplers that may be used in the oxidation dye compositions in accordance with the invention may be chosen from the couplers conventionally used in oxidation dyeing, and among which mention may be made especially of meta-phenylenediamines, meta-aminophenols, meta-diphenols, mono- or polyhydroxylated naphthalene derivatives and heterocyclic couplers such as, for example, indole or pyridine derivatives, and the addition salts thereof.

These couplers are chosen more particularly from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl-amino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof.

When they are present, these couplers especially represent from 0.0001% to 10% of the total weight of the dye composition, preferably from 0.005% to 5% by weight and even more preferably from 0.1% to 3% of this weight.

In general, the addition acid salts that may be used in the context of the dye compositions of the invention (oxidation bases and couplers) are chosen especially from the hydrochlorides, hydrobromides, sulfates, tartrates, lactates and acetates. The addition base salts are especially those obtained with sodium hydroxide, potassium hydroxide, ammonia, amines or alkanolamines.

The medium that is suitable for dyeing (or support) used according to the invention consists of water or of a mixture of water and at least one organic solvent chosen from $C_1$–$C_4$ lower alkanols, polyols and polyol ethers, aromatic alcohols, similar products and mixtures thereof.

The dye composition according to the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, reducing agents, sunscreens, penetrating agents, sequestering agents, fragrances, buffers, dispersants, conditioners, for instance silicones, film-forming agents, preserving agents and opacifiers.

The pH of the dye composition according to the invention is between 3 and 12.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels, or in any other form that is suitable for dyeing keratin fibers, and especially human hair.

Another subject of the invention is a process for dyeing keratin fibers, and in particular human keratin fibers such as the hair, using the dye composition as defined above.

According to this process, at least one dye composition as defined above is applied to the fibers, for a time that is sufficient to develop the desired coloration, either in air or using an oxidizing agent. The dye composition may optionally contain oxidation catalysts, so as to accelerate the oxidation process.

According to a first embodiment of the process of the invention, the coloration of the fibers may be performed without adding an oxidizing agent, solely by contact with atmospheric oxygen.

According to a second embodiment of the process of the invention, at least one dye composition as defined above is applied to the fibers, the color being revealed at acidic, neutral or alkaline pH using an oxidizing agent that is added to the composition just at the time of use, or which is present in an oxidizing composition applied simultaneously or sequentially in a separate manner.

According to this second embodiment of the dyeing process of the invention, the dye composition described above is preferably mixed, at the time of use, with an oxidizing composition containing, in a medium that is suitable for dyeing, at least one oxidizing agent present in an amount that is sufficient to develop a coloration. The mixture obtained is than applied to the keratin fibers and is left for an action time of 3 to 50 minutes and preferably 5 to 30 minutes, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulfates. Hydrogen peroxide is particularly preferred.

The pH of the oxidizing composition containing the oxidizing agent as defined above is such that, after mixing with the dye composition, the pH of the resulting composition applied to the keratin fibers preferably ranges between 3 and 12, and even more preferably between 5 and 11. It is adjusted to the desired value by means of acidifying or basifying agents usually used in the dyeing of keratin fibers, and as defined above.

The oxidizing composition as defined above may also contain various adjuvants conventionally used in compositions for dyeing the hair and as defined above.

The composition that is finally applied to the keratin fibers may be in various forms, such as in the form of liquids, creams or gels, or in any other form that is suitable for dyeing keratin fibers, and especially human hair.

Another subject of the invention is a multi-compartment device or dyeing "kit" or any other multi-compartment packaging system, a first compartment of which contains the dye composition as defined above, and a second compartment of which contains the oxidizing composition as defined above. These devices may be equipped with a means for applying the desired mixture to the hair, such as the devices described in patent FR-2 586 913 in the name of the Applicant.

The examples that follow are intended to illustrate the invention without, however, limiting its scope.

EXAMPLES OF SYNTHESIS

Synthesis of 1-[4-amino-2-(2-hydroxyethyl)-2H-pyrazol-3-yl]pyrrolidin-3-ol dihydrobromide (5)

Synthesis of 3,4,5-tribromopyrazole (1)

An aqueous solution (350 ml) containing sodium hydroxide (24 g, 0.6 mol) and pyrazole (10 g, 0.147 mol) was prepared with stirring.

After cooling the reaction medium to 20° C., $Br_2$ (72 g, 0.45 mol) was added dropwise over 1 hour, while maintaining the temperature between 20° C. and 25° C. The reaction was monitored by thin layer chromatography (TLC) (50% hexane/50% EtOAc or ethyl acetate). The precipitate was filtered off and washed with demineralized water (100 ml). The filtrate was acidified to pH 6–7 using HCl (10%, 33 g, 0.27 mol) and maintaining the temperature between 20 and 25° C. The precipitate thus formed was filtered off and washed with demineralized water (100 ml). The combined solids were maintained at reflux in Dean-Stark apparatus in the presence of toluene (200 ml). At the end of collection of the water, the organic phase was filtered while hot. The solvent was evaporated down to a residual volume of 110 ml. The solution was cooled to 0–5° C. for 1 hour. The precipitate formed was collected by filtration, washed with cold toluene (20 ml) and dried under vacuum at 80° C. to give the 3,4,5-tribromopyrazole (1) in the form of an off-white solid (30 g, 67%).

$^{13}C$ NMR (100 MHz, $d_6$-DMSO): 97.7–116.1–126.4 melting point: 182–184° C.

Synthesis of 3,5-dibromo-4-nitropyrazole (2)

$HNO_3$ (d=1.50 g/ml; 18 ml, 0.429 mol) was added dropwise over 10 minutes to a solution of 3,4,5-tribromopyrazole (1) (50 g, 0.164 mol) in glacial acetic acid (750 ml) while maintaining the temperature at 15° C. Acetic anhydride (250 ml) was added and the reaction mixture was stirred at room temperature for 2 hours. Once the reaction was complete, the reaction mixture was poured onto crushed ice (1 kg). After stirring for 1 hour, the crude product was filtered off and then washed with demineralized water (2×60 ml) to give crude 1-nitro-3,4,5-tribromopyrazole. The water (24.6 ml) contained in the wet product was removed by heating a solution of the product in toluene (750 ml) at reflux in Dean-Stark apparatus. The toluene solution was maintained at reflux for a further 30 minutes until a TLC (eluent:toluene) showed that the rearrangement of the 1-nitro-3,4,5-tribromopyrazole (Rf=0.77), the intermediate formed, into 3,5-dibromo-4-nitropyrazole 2 (Rf=0.05) was complete. The solution was concentrated to a residual volume of 150 ml and then cooled to 60° C., followed by addition of hexane (275 ml). The solution was cooled to 0–5° C. for 1 hour and the 3,5-dibromo-4-nitropyrazole (2) (29.1 g, 65%) was recovered, by filtration and drying under vacuum in the form of a pale yellow solid.

melting point: 127.6–130.1° C.

Synthesis of 2-(3,5-dibromo-4-nitropyrazol-1-yl)ethanol (3)

A solution of 3,5-dibromo-4-nitropyrazole (2) (11.0 g, 41 mmol) in DMF (52 ml) was added dropwise over 20 min to a stirred solution of NaH (1.76 g, 46 mmol; 60% dispersion in oil, prewashed with hexane under an inert atmosphere) in DMF (88 ml). After stirring for 10 minutes, a solution of 2-bromoethanol (6.4 g, 49 mmol) in DMF (14 ml) was added dropwise over 10 minutes. The reaction mixture was heated to 80° C. for 2 hours and then the DMF was evaporated off under reduced pressure. A mixture of DCM/water (100 ml, 1/1) is added to the residue and the organic phase is washed with water (50 ml). The organic phase was dried over $Na_2SO_4$ and the solvent was evaporated off under reduced pressure. The crude brown solid obtained was subsequently purified by column chromatography (5%/95% EtOAc/hexane). The yellow solid product (3.4 g) was recrystallized from a mixture of toluene/hexane (20 ml, 55%/45%) to give the 2-(3,5-dibromo-4-nitropyrazol-1-yl)ethanol (3) in the form of a white solid (2.8 g, 22%).

melting point: 102.5–104.8° C.
elemental analysis:
found: C: 19.29%, H: 1.50%, N: 12.99%, Br: 50.69%
theory: C: 19.07%, H: 1.60%, N: 13.34%, Br: 50.75%:
$^1$H NMR (400 MHz, $CDCl_3$): 41 (2 H, t, J=5.0 Hz, $NCH_2CH_2O$), 4.11 (2 H, t, J=5.0 Hz, $NCH_2CH_2O$), 2.13 (1 H, s, OH).

Synthesis of 1-[5-bromo-2-(2-hydroxyethyl)-4-nitro-2H-pyrazol-3-yl]pyrrolidin-3-ol (4)

A mixture of 2-(3,5-dibromo-4-nitropyrazol-1-yl)ethanol (3) (6.5 g, 21 mmol) and pyrrolidinol (3.75 g, 42 mmol) in EtOH (130 ml) was heated at 60° C. for 15 hours. The reaction was stopped after 67% conversion (monitoring by TLC and HPLC) by evaporating off the solvent under reduced pressure at 40° C. (rotary evaporator). The liquid obtained was purified by column chromatography (gradient of from 5%/95% EtOAc/hexane to 20%/80% EtOAc/hexane). The yellow solid obtained (3.9 g) was recrystallized from EtOH to give 1-[5-bromo-2-(2-hydroxyethyl)-4-nitro-2H-pyrazol-3-yl]pyrrolidin-3-ol (4) in the form of a yellow solid (3.5 g, 53%).

melting point: 90.4–92.6° C.
$^1$H NMR (400 MHz, $CDCl_3$): 4.62 (1 H, m, CH(OH)); 4.32(2 H, q, J=5.0 Hz, $NCH_2CH_2O$); 4.03 (2 H, $S_{broad}$, $NCH_2CH_2O$); 3.60 (1 H, dd, J=11.0 Hz and 4.0 Hz, $NCH_2CH(OH)$); 3.56 (1 H, dd, J=9.0 Hz and 8.0 Hz, $CH_2CH_2CH(OH)$); 3.34 (1 H, ddd, J=9.0 Hz and 8.5 Hz and 4.0 Hz; $CH_2CH_2CH(OH)$); 3.19 (1 H, d, $J_{gem}$=11.0 Hz, $NCH_2CH(OH)$); 2.48 (1H, $S_{broad}$, OH); 2.31 (1 H, m, $CH_2CH_2CH(OH)$); 2.30 (1 H, $S_{broad}$, OH); 2.05 (1 H, m, $CH_2CH_2CH(OH)$).

Synthesis of 1-[4-amino-2-(2-hydroxyethyl)-2H-pyrazol-3-yl]pyrrolidin-3-ol hydrobromide (5)

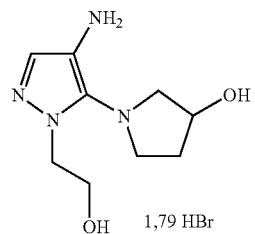

A mixture of 1-[5-bromo-2-(2-hydroxyethyl)-4-nitro-2H-pyrazol-3-yl]pyrrolidin-3-ol (4) (5.0 g, 16 mmol) in EtOH (500 ml) and Pd/C (10%, 1.15 g wet, 0.5 g dry, Johnson-Matthey Type 487) containing HBr (48%, 6.0 g, 32 mmol) was hydrogenated in a 1 L Parr autoclave at 12 bar for 15 hours. The catalyst was filtered off and washed with EtOH (50 ml), and the combined alcoholic phases were evaporated under reduced pressure to give a red oil (7.3 g). Under inert atmosphere, the oil was taken up in isopropanol (20 ml) and heated until the solution appeared uniform. Acetone (140 ml) was added until the product precipitated. After leaving this solution to stand in the cold for 15 hours, the solid was recovered by filtration and dried under reduced pressure at 60° C. to give the 1-[4-amino-2-(2-hydroxyethyl)-2H-pyrazol-3-yl]pyrrolidin-3-ol (5) (1.8 g, 24%), isolated as the hydrobromide, in the form of a beige-colored solid.

melting point: 136–138.2° C.
elemental analysis: C9H16N4O2 (1.79 eq. HBr); MW=357.10 g/mol
found: C: 30.71%, H: 5.01%, N: 13.12%, Br: 37.65%
theory: C: 28.89%, H: 4.85%, N: 14.97%, Br: 42.72%
$^1$H NMR (400 MHz, $CDCl_3$): 13.90 (1H, s, NH); 9.70 (1 H, s, NH); 7.86 (1 H, s, $H_{Ar}$), 4.35 (1 H, m, CH(OH)); 4.08–4.01 (4 H, m, $NCH_2CH_2OH$ and $NCH_2CH_2OH$); 3.73 (1 H, m, $NCH_2CH(OH)$); 3.40 (1 H, m, $CH_2CH_2CH(OH)$); 3.28 (1 H, m, $CH_2CH_2CH(OH)$); 3.05 (1 H, dd, $NCH_2CH(OH)$); 2.09–2.00 (2 H, m, $CH_2CH_2CH(OH)$); 1.86 (1 H, $S_{broad}$, OH)

FORMULATION EXAMPLES 1 TO 3 (Dyeing in Alkaline Medium)

| The dye formulations-below are prepared: | |
|---|---|
| 4,5-diaminopyrazole of formula (I) | 5 × 10$^{-3}$ mol |
| coupler | 5 × 10$^{-3}$ mol |
| oleyl alcohol polyglycerolated with 2 mol of glycerol | 4.0 g |
| oleyl alcohol polyglycerolated with 4 mol of glycerol, containing 78% active material (A.M.) | 5.7 g A.M. |
| oleic acid | 3.0 g |
| oleylamine containing 2 mol of ethylene oxide, sold under the trade name Ethomeen O12 by the company Akzo | 7.0 g |
| diethylaminopropyl laurylamino succinamate, sodium salt, at 55% A.M. | 3.0 g A.M. |
| oleyl alcohol | 5.0 g |
| oleic acid diethanolamide | 12.0 g |
| propylene glycol | 3.5 g |
| ethyl alcohol | 7.0 g |
| dipropylene glycol | 0.5 g |
| propylene glycol monomethyl ether | 9.0 g |
| sodium metabisulfite as an aqueous solution containing 35% A.M. | 0.455 g A.M. |
| ammonium acetate | 0.8 g |
| antioxidant, sequestering agent | qs |
| fragrance, preserving agent | qs |
| aqueous ammonia containing 20% $NH_3$ | 10 g |
| The pH of the composition is 9.5 | |
| A.M. means "active material" | |

| Example | Base | Coupler |
|---|---|---|
| 1 | 1-[4-Amino-2-(2-hydroxyethyl)-2H-pyrazol-3-yl]-pyrrolidin-3-ol, 1.79HBr (5) | 5-amino-6-chloro-2-methylphenol, HCl |

-continued

| Example | Base | Coupler |
|---|---|---|
| 2 | 1-[4-Amino-2-(2-hydroxy-ethyl)-2H-pyrazol-3-yl]-pyrrolidin-3-ol, 1.79HBr (5) | 2-methyl-5-amino-phenol |
| 3 | 1-[4-Amino-2-(2-hydroxy-ethyl)-2H-pyrazol-3-yl]-pyrrolidin-3-ol, 1.79HBr (5) | 1 β-hydroxyethoxy-2,4-diaminobenzene, 2HCl |

At the time of use, each dye composition is mixed, weight for weight, with a 20-volumes aqueous hydrogen peroxide solution (6% by weight), the pH of which has been adjusted to about 2.5 with orthophosphoric acid.

The mixture is applied to natural or permanent-waved grey hair containing 90% white hairs. The hair is then rinsed, washed with a standard shampoo, rinsed and dried.

The color of the locks was evaluated in the L*a*b* system, on white and permanent-waved hair, using a Minolta CM 2002 spectrophotometer.

In the L*a*b* space, the lightness is indicated by the value L* on a scale from 0 to 100, while the chromatic data is expressed by a* and b* which indicate two color axes, a* the red-green axis and b* the yellow-blue axis.

According to this system, the higher the value of L, the paler and less intense the color. Conversely, the lower the value of L, the darker or more intense the color.

| | Natural white hair | | | Permanent-waved white hair | | |
|---|---|---|---|---|---|---|
| Example | L* | a* | b* | L* | a* | b* |
| Example 1 | 46.5 | 15.5 | −1.20 | 36.7 | 23.7 | −6.25 |
| Example 2 | 51.9 | 16.1 | −5.45 | 40.9 | 21.8 | 3.6 |
| Example 3 | 43.9 | 2.8 | −0.45 | 30.6 | 4.6 | −6.9 |

The 4,5-diaminopyrazoles according to the invention thus make it possible to obtain strong and chromatic shades at alkaline pH.

The invention claimed is:

1. A diaminopyrazole compound having the following structure (I), and the physiologically acceptable salts thereof:

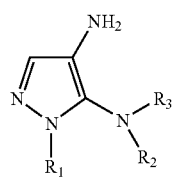

(I)

wherein:
$R_1$ is chosen from linear and branched $C_1$–$C_6$ alkyl groups and linear and branched $C_2$–$C_6$ alkenyl groups, comprising at least one substituent chosen from OR, $C_1$–$C_4$ alkoxy, NRR', SR, SOR, $SO_2R$, COOR, CONRR', PO(OH)$_2$, $SO_3X$, NHCONRR', a non-cationic heterocycle, an aryl group and a halogen;
$R_2$ and $R_3$, which may be identical or different, are other than H and are chosen from linear and branched, substituted and unsubstituted $C_1$–$C_6$ alkyl and $C_2$–$C_6$ alkenyl groups, wherein $R_2$ and $R_3$ may form with the nitrogen atom to which they are attached a saturated or unsaturated, at least 4-membered heterocycle, optionally comprising at least one further hetero atom chosen from N, O and S,
wherein $R_2$, $R_3$ or said heterocycle optionally being substituted with at least one substituent chosen from OR, NRR', SR, SOR, $SO_2R$, COOR, CONRR', PO(OH)$_2$, $SO_3X$, NHCONRR', a non-cationic heterocycle, an aryl group and a halogen, and said heterocycle optionally being substituted with at least one substituent further chosen from CHO, phenyl, and saturated or unsaturated 5- or 6-membered heterocycles comprising at least one hetero atom,
wherein R and R', which may be identical or different, are chosen from a hydrogen atom, a linear and branched $C_1$–$C_6$ alkyl group optionally substituted with OH, a linear and branched $C_2$–$C_6$ alkenyl group, and a $C_1$–$C_4$ alkoxy group substituted with a substituent chosen from OH and NR"R"', where R" and R"', which may be identical or different, are chosen from hydrogen and a $C_1$–$C_4$ alkyl group; or
R and R' may form, with the nitrogen atom to which they are attached, an at least 4-membered heterocycle optionally comprising at least one additional hetero atom chosen from O, N and S, wherein R, R' and said at least 4-membered heterocycle are unsubstituted or substituted; and
X is chosen from a hydrogen atom, alkali metal atoms, alkaline-earth metal atoms, and ammonium groups.

2. The compound of claim 1, wherein $R_1$ is chosen from linear and branched $C_1$–$C_4$ alkyl groups and linear and branched $C_2$–$C_4$ alkenyl groups, comprising at least one substituent chosen from OR, NRR', SR, SOR, $SO_2R$, COOR, CONRR', PO(OH)$_2$, $SO_3X$, NHCONRR', a non-cationic heterocycle, an aryl group and a halogen.

3. The compound of claim 1, wherein $R_2$ and $R_3$ are chosen from substituted or unsubstituted, linear or branched $C_1$–$C_4$ alkyl groups and $C_2$–$C_4$ alkenyl groups as defined in claim 1.

4. The compound of claim 1, wherein R and R' are chosen from linear or branched $C_1$–$C_4$ alkyl groups and $C_2$–$C_4$ alkenyl groups as defined in claim 1.

5. The compound of claim 1, wherein the physiologically acceptable salts are acid salts chosen from hydrochlorides, hydrobromides, sulfates, tartrates, lactates and acetates.

6. The compound of claim 1, wherein the physiologically acceptable salts are base salts chosen from sodium hydroxide, potassium hydroxide, ammonia, amines and alkanolamines.

7. The compound of claim 1, wherein $R_1$ is chosen from a linear and branched $C_1$–$C_6$ alkyl group substituted with a substituent chosen from $SO_3H$, COOH, $CONH_2$, OH, $C_1$–$C_4$ alkoxy, $NH_2$ and NRR' groups;
R and R', which may be identical or different, are chosen from a $C_1$–$C_4$ alkyl group, which is optionally substituted with OH, and a $C_1$–$C_4$ alkoxy group substituted with a substituent chosen from OH and NR"R"', where R" and R"', which may be identical or different, are chosen from hydrogen and a $C_1$–$C_4$ alkyl group; or
R and R' may form with the nitrogen atom to which they are attached a 5- or 6-membered heterocycle optionally comprising at least one hetero atom chosen from O and N.

8. The compound of claim 1, wherein $R_2$ and $R_3$, which may be identical or different, are chosen from $C_1$–$C_6$ alkyl groups optionally substituted with a substituent chosen from OH, $NH_2$, a $C_1$–$C_6$ alkoxy group, and COOH; or $R_2$ and $R_3$ may form with the nitrogen atom to which they are attached a 5- or 6-membered heterocycle optionally comprising at least one hetero atom chosen from O and N, said heterocycle optionally being substituted with at least one substituent chosen from CHO, $CONH_2$, OH, $NH_2$, phenyl, and saturated or unsaturated 5- or 6-membered heterocycles optionally comprising at least one hetero atom, or at least one $CO_2R''$ group in which $R''$ is chosen from H and a $C_1$–$C_4$ alkyl group.

9. The compound of claim 8, wherein the saturated or unsaturated 5- or 6-membered heterocycle optionally comprises at least one hetero atom chosen from O and N.

10. A composition for the oxidation dyeing of keratin fibers, comprising, in a medium suitable for dyeing, as an oxidation base, at least one 4,5-diaminopyrazole compound having the following structure (I), and the physiologically acceptable salts thereof:

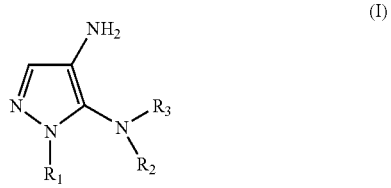

(I)

wherein $R_1$ is chosen from linear and branched $C_1$–$C_6$ alkyl groups and linear and branched $C_2$–$C_6$ alkenyl groups, wherein $R_1$ comprises at least one substituent chosen from OR, NRR', SR, SOR, $SO_2R$, COOR, CONRR', $PO(OH)_2$, $SO_3X$, NHCONRR', a non-cationic heterocycle, an aryl group, and a halogen;

$R_2$ and $R_3$, which may be identical or different, are other than H and are chosen from linear and branched, substituted and unsubstituted $C_1$–$C_6$ alkyl and $C_2$–$C_6$ alkenyl groups, or $R_2$ and $R_3$ may form with the nitrogen atom to which they are attached a saturated or unsaturated, at least 4-membered heterocycle, optionally comprising at least one further hetero atom chosen from N, O and S, $R_2$, $R_3$ or said heterocycle optionally being substituted with at least one substituent chosen from OR, NRR', SR, SOR, $SO_2R$, COOR, CONRR', $PO(OH)_2$, $SO_3X$, NHCONRR', a non-cationic heterocycle, an aryl group, and a halogen, and said heterocycle optionally being substituted with at least one substituent further chosen from CHO, phenyl, and saturated or unsaturated 5- or 6-membered heterocycles comprising at least one hetero atom, wherein R and R', which may be identical or different, are chosen from a hydrogen atom, a linear and branched $C_1$–$C_6$ alkyl group and a linear and branched $C_2$–$C_6$ alkenyl group; or R and R' may form, with the nitrogen atom to which they are attached, an at least 4-membered heterocycle optionally comprising at least one additional hetero atom chosen from O, N and S, wherein R, R' or said at least 4-membered heterocycle are unsubstituted or substituted; and X is chosen from a hydrogen atom, alkali metal atoms, alkaline-earth metal atoms and ammonium groups.

11. The composition of claim 10, wherein the keratin fibers are human hair.

12. The composition of claim 10, wherein $R_1$ is chosen from linear and branched $C_1$–$C_4$ alkyl groups and linear and branched $C_2$–$C_4$ alkenyl groups, comprising at least one substituent chosen from OR, NRR', SR, SOR, $SO_2R$, COOR, CONRR', $PO(OH)_2$, $SO_3X$, NHCONRR', a non-cationic heterocycle, an aryl group, and a halogen.

13. The composition of claim 10, wherein $R_2$ and $R_3$ are chosen from linear and branched, substituted and unsubstituted $C_1$–$C_4$ alkyl and $C_2$–$C_4$ alkenyl groups, $R_2$ and $R_3$ optionally being substituted with at least one substituent chosen from OR, NRR', SR, SOR, $SO_2R$, COOR, CONRR', $PO(OH)_2$, $SO_3X$, NHCONRR', a non-cationic heterocycle, an aryl group, and a halogen.

14. The composition of claim 10, wherein R and R', which may be identical or different, are chosen from linear and branched $C_1$–$C_4$ alkyl and $C_2$–$C_4$ alkenyl groups as defined in claim 10.

15. The composition of claim 10, wherein the diaminopyrazole compound of formula (I) or physiologically acceptable salts thereof are present in an amount ranging from 0.001% to 10% by weight of said composition.

16. The composition of claim 15, wherein the diaminopyrazole compound of formula (I) or physiologically acceptable salts thereof are present in an amount ranging from 0.05% to 6% by weight of said composition.

17. The composition of claim 16, wherein the diaminopyrazole compound of formula (I) or physiologically acceptable salts thereof are present in an amount ranging from 0.1% to 3% by weight of said composition.

18. The composition of claim 10, wherein the medium suitable for dyeing comprises water or a mixture of water and at least one organic solvent chosen from $C_1$–$C_4$ alkanols, polyols, polyol ethers, and aromatic alcohols.

19. The composition of claim 10, having a pH ranging from 3 to 12.

20. The composition of claim 10, further comprising at least one additional oxidation base chosen from para-phenylenediamines, bis(phenyl)alkylenediamines, para-aminophenols, ortho-aminophenols and heterocyclic bases other than the diaminopyrazole compound of formula (I), and addition salts thereof with an acid.

21. The composition of claim 20, wherein the at least one additional oxidation base is present in an amount ranging from 0.0005% to 12% by weight relative to the total weight of the composition.

22. The composition of claim 10, comprising at least one additional component chosen from at least one coupler and at least one direct dye.

23. The composition of claim 22, wherein the at least one coupler is chosen from meta-phenylenediamines, meta-aminophenols, meta-diphenols, monohydroxylated naphthalene derivatives, polyhydroxylated naphthalene derivatives and heterocyclic couplers, and the addition salts thereof with an acid.

24. The composition of claim 22, wherein the at least one coupler is present in an amount ranging from 0.0001% to 10% by weight relative to the total weight of the composition.

25. The composition of claim 10, wherein the physiologically acceptable salts comprise acid salts chosen from hydrochlorides, hydrobromides, sulfates, tartrates, lactates and acetates, and base salts chosen from those obtained with sodium hydroxide, potassium hydroxide, ammonia and amines.

26. A process for dyeing keratin fibers comprising applying at least one dye composition to the keratin fibers, for a time that is sufficient to develop a desired coloration, either in air or using an oxidizing agent, optionally in the presence of at least one oxidation catalyst,
  wherein the dye composition comprises, in a medium suitable for dyeing, as an oxidation base, at least one 4,5-diaminopyrazole compound having the following structure (I), and the physiologically acceptable salts thereof:

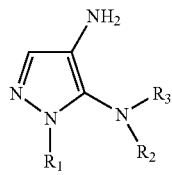

in which
  $R_1$ is chosen from linear and branched $C_1$–$C_6$ alkyl groups and linear and branched $C_2$–$C_6$ alkenyl groups, wherein $R_1$ comprises at least one substituent chosen from OR, NRR', SR, SOR, $SO_2R$, COOR, CONRR', $PO(OH)_2$, $SO_3X$, NHCONRR', a non-cationic heterocycle, an aryl group, and a halogen;
  $R_2$ and $R_3$, which may be identical or different, are other than H and are chosen from linear and branched, substituted and unsubstituted $C_1$–$C_6$ alkyl and $C_2$–$C_6$ alkenyl groups, $R_2$ and $R_3$ may form with the nitrogen atom to which they are attached a saturated or unsaturated, at least 4-membered heterocycle, optionally comprising at least one further hetero atom chosen from N, O and S or
  $R_2$, $R_3$ or said heterocycle optionally being substituted with at least one substituent chosen from OR, NRR', SR, SOR, $SO_2R$, COOR, CONRR', $PO(OH)_2$, $SO_3X$, NHCONRR', a non-cationic heterocycle, an aryl group and a halogen, and said heterocycle optionally being substituted with at least one substituent further chosen from CHO, phenyl, and saturated or unsaturated 5- or 6-membered heterocycles comprising at least one hetero atom,
    wherein R and R', which may be identical or different, are chosen from a hydrogen atom, a linear and branched $C_1$–$C_6$ alkyl group, and a linear and branched $C_2$–$C_6$ alkenyl group; or
    R and R' may form, with the nitrogen atom to which they are attached, an at least 4-membered heterocycle optionally comprising at least one additional hetero atom chosen from O, N and S, wherein R, R' or said at least 4-membered heterocycle are unsubstituted or substituted; and
    X is chosen from a hydrogen atom, alkali metal atoms, alkaline-earth metal atoms and ammonium groups.

27. The process of claim 26, wherein the coloration is revealed solely on contact with atmospheric oxygen.

28. The process of claim 27, wherein said color is revealed at acid, neutral, or alkaline pH with the aid of the oxidizing agent, said oxidizing agent being added to the dye composition just at the time of application, or which is present in an oxidizing composition applied simultaneously or sequentially to the keratin fibers.

29. The process of claim 26, wherein the keratin fibers are human hair.

30. The process of claim 26, wherein the oxidizing agent is chosen from hydrogen peroxide, urea peroxide, alkali metal bromates and persalts.

31. The process of claim 30, wherein the persalts are chosen from perborates and persulfates.

32. A multi-compartment device or multi-compartment dyeing kit, comprising
  a first compartment containing a dye composition comprising, in a medium suitable for dyeing, as an oxidation base, at least one 4,5-diaminopyrazole compound having the following structure (I), and the physiologically acceptable salts thereof:

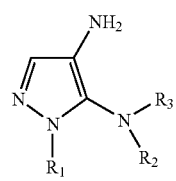

wherein,
  $R_1$ is chosen from linear and branched $C_1$–$C_6$ alkyl groups and linear or branched $C_2$–$C_6$ alkenyl groups, wherein $R_1$ comprises at least one substituent chosen from OR, NRR', SR, SOR, $SO_2R$, COOR, CONRR', $PO(OH)_2$, $SO_3X$, NHCONRR', a non-cationic heterocycle, an aryl group, and a halogen;
  $R_2$ and $R_3$, which may be identical or different, are other than H and are chosen from linear and branched, substituted and unsubstituted $C_1$–$C_6$ alkyl and $C_2$–$C_6$ alkenyl groups or $R_2$ and $R_3$ may form with the nitrogen atom to which they are attached a saturated or unsaturated, at least 4-membered heterocycle, optionally comprising at least one further hetero atom chosen from N, O and S,
  $R_2$, $R_3$ or said heterocycle optionally being substituted with at least one substituent chosen from OR, NRR', SR, SOR, $SO_2R$, COOR, CONRR', $PO(OH)_2$, $SO_3X$, NHCONRR', a non-cationic heterocycle, an aryl group, and a halogen, and said heterocycle optionally being substituted with at least one substituent further chosen from CHO, phenyl, and saturated or unsaturated 5- or 6-membered heterocycles comprising at least one hetero atom,
  wherein R and R', which may be identical or different, are chosen from a hydrogen atom, a linear and branched $C_1$–$C_6$ alkyl group and a linear and branched $C_2$–$C_6$ alkenyl group; or
  R and R' may form, with the nitrogen atom to which they are attached, an at least 4-membered heterocycle optionally comprising at least one additional hetero atom chosen from O, N and S, wherein R, R' or said at least 4-membered heterocycle are unsubstituted or substituted; and
  X is chosen from a hydrogen atom, alkali metal atoms, alkaline-earth metal atoms and ammonium groups.

* * * * *

UNITED STATES PATENT AND TRADEMARK OFFICE
CERTIFICATE OF CORRECTION

PATENT NO. : 7,091,350 B2 Page 1 of 1
APPLICATION NO. : 10/468300
DATED : August 15, 2006
INVENTOR(S) : Thilo Fessmann and Eric Terranova It is certified that error appears in the above-identified patent and that said Letters Patent is hereby corrected as shown below:

On the title page, item (57), in the Abstract, line 21, "same" should read --same.--.

In claim 26, column 37, line 29, "groups, $R_2$" should read --groups, or $R_2$--.

In claim 26, column 37, line 33, "S or" should read --S,--.

In claim 32, column 38, line 36, "groups or" should read --groups, or--.

Signed and Sealed this

Fourteenth Day of November, 2006

JON W. DUDAS
*Director of the United States Patent and Trademark Office*